United States Patent [19]

Tischer et al.

[11] Patent Number: 4,910,135

[45] Date of Patent: Mar. 20, 1990

[54] WATER-SOLUBLE PEROXIDASE DERIVATIVES

[75] Inventors: Wilhelm Tischer, Peissenberg; Josef Heinle, Munich; Michael-Harold Town, Oberhausen, all of Fed. Rep. of Germany

[73] Assignee: Boehringer Mannheim GmbH, Mannheim, Fed. Rep. of Germany

[21] Appl. No.: 930,871

[22] Filed: Nov. 14, 1986

[30] Foreign Application Priority Data

Nov. 21, 1985 [DE] Fed. Rep. of Germany ....... 3541186

[51] Int. Cl.$^4$ ..................... C12Q 1/28; C12N 11/02; C12N 11/06; C12N 9/96
[52] U.S. Cl. ..................... 435/28; 435/188; 435/177; 435/178; 435/180; 435/181
[58] Field of Search ............... 435/28, 177, 178, 179, 435/180, 181, 182, 188; 436/66

[56] References Cited

U.S. PATENT DOCUMENTS

| | | | |
|---|---|---|---|
| 3,860,484 | 1/1975 | O'Malley | 195/63 |
| 4,138,292 | 2/1979 | Chibata et al. | 435/178 |
| 4,320,194 | 3/1982 | Bull | 435/7 |
| 4,460,683 | 7/1984 | Gloger et al. | 435/10 |
| 4,634,671 | 1/1987 | Sakata et al. | 435/188 |
| 4,652,524 | 3/1987 | Modrovich et al. | 435/188 |

OTHER PUBLICATIONS

Nakane, P. K., and A. Kawaoi., J. Histochem. Cytochem., vol. 22, No. 12, pp. 1084–1091 (1974).
Ishikawa et al., J. Immunoassay, vol. 4, No. 3, pp. 216–218 (1983).

*Primary Examiner*—Robert J. Warden
*Assistant Examiner*—Toni R. Scheiner
*Attorney, Agent, or Firm*—Felfe & Lynch

[57] ABSTRACT

A water-soluble peroxidase derivative obtainable by the oxidation of peroxidase with periodic acid or with a salt thereof and binding to a water-soluble polymer selected from polysaccharides, polyethylene glycols, polyvinylpyrrolidones and polyacid anhydrides. Also provided is a process for the preparation of this water-soluble peroxidase derivative and for the use of this water-soluble peroxidase derivative for the determination of hydrogen peroxide.

14 Claims, No Drawings

WATER-SOLUBLE PEROXIDASE DERIVATIVES

The present invention is concerned with a water-soluble, stabilized peroxidase (POD), with a process for the preparation thereof and with the use thereof for the determination of hydrogen peroxide.

Peroxidase (E.C. 1.11.1.7) is an enzyme which is frequently used in diagnostic reagents. It is particularly used for the determination of hydrogen peroxide which has been formed in oxidase-catalysed reactions. An oxidating coupling of color components hereby takes place to give a colored product, the amount of which gives a quantitative conclusion for the enzyme or substrate to be determined.

POD is substantially stable in buffer solutions, i.e. the activity does not decrease or only decreases slightly even after storage for several days. However, in the reagent compositions usually employed in clinical chemistry, which contain detergents and/or complex formers, for example ethtlenediamine-tetraacetic acid (EDTA), losses of >90% of the activity can be reckoned with after 6 days at ambient temperature. In order to ensure that the POD activity is still present in sufficient amount even after such reagents have been stored for several days, peroxidase is usually employed in a several fold excess.

However, an important disadvantage of such high POD concentrations is that considerable reagent blank values arise. This is caused by hem groups which the enzyme contains and which absorb light in the visible range. This results in precision loss for the measurement results.

From Federal Republic of Germany Patent Specification No. 29 19 622 is known a process for the preparation of water-soluble enzyme derivatives which are stable in detergent-containing solutions. In this case, the enzymes are reacted with aldehyde group-containing polysaccharide derivatives. However, on contradistinction to other enzymes modified in this way which can thus be stabilized, peroxidase modified in this manner does not show a sufficiently improved stability in solutions containing detergents and/or complex formers.

Consequently, it is an object of the present invention to provide a water-soluble peroxidase derivative, the activity of which is maintained for a comparatively long time in aqueous solutions containing detergents and/or complex formers.

Thus, according to the present invention, there is provided a water-soluble peroxidase derivative which is obtainable by oxidizing peroxidase with periodic acid or a salt thereof and binding to a water-soluble polymer which is a polysaccharide, polyethylene glycol, polyvinylpyrrolidone or polyacid anhydride.

Surprisingly, we have found that POD derivatives modified in this way display an excellent long-term stability in solutions containing detergents and/or complex formers without important enzyme properties being lost.

The oxidation of the peroxidase takes place under known conditions with periodic acid or with a salt thereof, especially an alkali metal salt. This is described, for example, in the scope of the preparation of peroxidase-antibody conjugates (see E. Ishkaa, J. Immunoassay, 4, 209–327/1983). The periodic acid or periodate is hereby preferably used in excess, a 20 to 200 fold excess being especially preferred. The temperature and pH value can vary within wide limits, preferably in the range of about 0°–30° C. and pH range of about 4–8. However, it has been found that the reaction takes place with especially good yields in a weakly acidic medium (pH 5 to 6) with cooling (0° to 10° C.). After carrying out the oxidation, it is advantageous to remove the oxidation agent by dialysis or chromatography, for example using "Sephadex"G-25.

In a further step, the oxidized enzyme is bound to a water-soluble polymer. The coupling with the polymer takes place in known manner by reacting the oxidized POD in aqueous solution with the dissolved polymer under defined conditions (cf., for example, European Patent Specification No. 0,069,379).

Suitable polymers are water-soluble polysaccharides, polyethylene glycols, polyvinylpyrrolidones and polyacid anhydrides. A preferred polysaccharide is dextran. However, good results are also obtained with other water-soluble polysaccharides and especially with soluble starch. High molecular weight polymers of mono- and disaccharides, such as are obtained, for example, by reaction with epihalohydrins (e.g. "Ficoll"), have also proved to be well suited. A copolymer of methyl vinyl ether with maleic anhydride has proved to be especially useful as a polyacid anhydride.

Sephadex is a chromatographic material and is defined as an insoluble dextran. Dextran T 40 is a dextran with an average molecular weight of 40 000. Ficoll is a saccharose polymerized with epichlorohydrine.

The binding of the oxidized POD to the polymer can take place without any further intermediate steps insofar as the polymer contains reactive groups, for example amino groups, which react with the oxidized POD. If the polymer does not contain any reactive groups, before reaction with the oxidized POD it is preferably activated and provided with reactive groups. Such methods are well known and are described, for example, in European Patent Specification No. 0,069,379 and by J.K. Inman in J. Immunol., 114, 704/1975).

For the activation of polysaccharides, it has proved to be advantageous to react them with cyanogen bromide, a 1-cyano-4-dimethylaminopyridinium salt (cDA) or 2,4,6-trichloro-1,3,5-triazine (TCT). Reaction with TCT is especially preferred for the activation of polyethylene glycol. For the activation of polymers containing carboxyl groups, they can be reacted with N-hydroxysuccinimide.

According to a preferred embodiment of the present invention, the oxidized POD is bound to the polymer via one or more alkylene radicals containing up to 8 carbon atoms in the molecule. For this purpose, the oxidized POD is reacted with an appropriate alkylenediamine and then bound to the possibly activated polymer. Ethylenediamine is especially preferred as alkylenediamine.

For stabilizing the binding with the alkylenediamine, it is especially advantageous, before the reaction with the polymer, to carry out a reduction step, preferably with boron hydride or cyanoboron hydride, and possibly to purify the modified enzyme by dialysis or chromatography.

The coupling is preferably carried out at a temperature of from 0° C. to ambient temperature at a pH of from 6 to 10. The mole ratio of enzyme to polymer can be varied within wide limits, for example from 1:1 to 1:20. However, especially high yields of coupling product are obtained with a mole ratio of about 1:4.

The isolation of the POD derivative according to the present invention can take place at the conclusion of the coupling reaction, for example by adding acetone and precipitating out. However, the solution obtained is preferably lyophilised, preferably after previous purification by dialysis or chromatography.

The derivatisation of the POD does not have any disadvantageous influence on the specificity and activity of the enzyme. On the contrary, it was, surprisingly, observed that the Michaelis constant (substrate hydrogen peroxide) of the POD derivatives according to the present invention is markedly smaller than that of the non-derivatised POD. The derivatives can advantageously be used for the determination of hydrogen peroxide, for example in reagents for clinical-chemical determinations (for example of uric acid). Due to the smaller Michaelis constant and the improved stability in reagent solutions containing detergent and/or complex former, the content of the POD derivatives according to the present invention can be considerably smaller than in the case of using non-derivatised POD.

The following Examples are given for the purpose of illustrating the present invention:

EXAMPLE 1

Binding of Activated Peroxidase to Dextran (a) Activation of the POD.

5 g. of horseradish peroxidase (E.C. 1.11.1.7) are dissolved in 250 ml. acetate buffer (30 mMole/liter; pH 5.5), 37.5 g. sodium periodate (0.2 mole/liter) are added thereto and the reaction mixture is incubated for 40 minutes at ambient temperature. Subsequently, 37.5 mol (1 mole/liter) ethylene glycol are added thereto and incubation continued for a further 20 minutes at ambient temperature. Thereafter, the reaction mixture is purified over a Sephadex G-25 column (elution agent: sodium acetate buffer; pH 5.5; 10 mmol/litre). (b) Reaction with ethylenediamine.

The pH value of the eluate is adjusted to 9.5 with 1 mole/litre sodium carbonate/sodium bicarbonate buffer (pH 9.8). Subsequently, 11.25 ml. (1 mole/liter) ethylenediamine solution (pH 9.5) are added thereto. The reaction mixture is then incubated for 1 hour at 22° C., the pH being maintained at 9.5 (pH stat) with the above-described carbonate/bicarbonate buffer.

The reaction mixture is adjusted to pH 8.0 with 1 mole/liter triethanolamine (TRA) buffer (pH 7.0). Subsequently, 750 mg. sodium cyanoboron hydride are added thereto and incubation carried out for 15 minutes at 22° C., the pH value being maintained at 8.0 (pH stat) with triethanolamine buffer. Thereafter, the reaction mixture is purified over a Sephadex G-25 column (elution agent: 10 mMole/liter phosphate buffer; pH 7.0).

(c) Binding to dextran.

The oxidised POD obtained according to (b) is bound to CDAP-BF$_4$-activated dextran T 40 according to the process described by J.J. Marshall (Preservation of enzymes by conjugation with dextran, American Chemical Society Symposium Series, 123, 125–140/1980) and modified by J. Kohn and M. Wilcheck (The use of cyanogen bromide and other novel cyanylating agents for the activation of polysaccharide resins, Appl. Biochem. Biotech., 9, 285–305/1984). There is obtained a specific POD activity of 15 to 18 U/mg.

EXAMPLE 2

Binding of Peroxidase to Ficoll

Peroxidase is derivatised as described in Example 1 and reacted with Ficoll instead of with dextran T 40.

There is obtained a yield of 25 to 30 g. of lyophilisate with a specific POD activity of 14 to 17 U/mg.

EXAMPLE 3

Binding to Aminodextran

The reaction mixture prepared according to Example 1(b) is mixed with 25 g. aminodextran (prepared according to J.K. Inman, J. Immunol., 114, 704/1975) (molecular weight about 40,000) and incubated for 2 hours at ambient temperature and at pH 9.3. Subsequently, it is reduced as in Example 1(b) at pH 8.0 with 750 mg. sodium borohydride and purified in the manner described in Example 1. There are obtained 25 to 30 g. of lyophilisate with a POD activity of 9 to 14 U/mg.

EXAMPLE 4

Binding of Native POD to Dextran (Comparison)

In the manner described in Example 1(c), horseradish peroxidase is bound directly to CDAP-BF$_4$-activated dextran T 40.

EXAMPLE 5

Comparison of the Stability of Various POD Derivatives

| enzyme | % residual activity in reagent a after 6 days at 20° C. |
|---|---|
| native POD | 4% |
| according to Example 4 | 11% |
| according to Example 3 | 64% |
| according to Example 2 | 70% |
| according to Example 1 | 70% |

Composition of reagent a:
0.1 mole/liter potassium phosphate buffer (pH 8.2)
0.1% sodium azide
0.1% ethylenediamine-tetraacetic acid
0.5% Lutensol ON 50 (non-ionic tenside from BASF)
7 mMole/liter sodium cholate It can be seen that the stability of non-derivatised (native) POD, as well as of POD fixed to dextran without derivatisation (Example 4) is only small, whereas the stability of POD which has been fixed to dextran after oxidation is markedly improved.

EXAMPLE 6

The stability of POD as investigated in dependence upon the addition of detergent and ethylenediaminetetraacetic acid. After a period incubation of 16 hours at 37° C., the following results were obtained:

| | residual activity | |
|---|---|---|
| reagent composition | native POD | POD according to Example 1 |
| 1. 0.1 mole/l. TRA buffer (pH 8.2) | 78% | 80% |
| 2. 1 + 0.1% EDTA[1] | 5% | 18% |
| 3. 0.1 mole/l. potassium phosphate buffer | 75% | 85% |
| 4. 3 + 0.5% Lutensol ON 50 + 7 mMole/l. sodium cholate[1] | 3% | 27% |
| 5. 3 + 0.1% EDTA | 23% | 57% |
| 6. 4 + 0.1% EDTA[1] | 8% | 43% |

[1]The investigations were carried out in the reagent mix together with other components (sodium azide and colouring materials).

EXAMPLE 7

The following Michaelis constants are obtained (substrate hydrogen peroxide) according to the Lineweaver-Burk method in the reagent mix according to

EXAMPLE 5

| enzyme | $K_M$ |
| --- | --- |
| native POD | $1.76 \times 10^{-5}$ |
| according to Example 1 | $7.12 \times 10^{-6}$ |

It will be understood that the specification and examples are illustrative but not limitative of the present invention and that other embodiments within the spirit and scope of the invention will suggest themselves to those skilled in the art.

What is claimed is:

1. A water soluble peroxidase derivative comprising peroxidase oxidized with periodic acid or a salt thereof and bound through one or more $C_1$-$C_8$ alkylene groups to a water-soluble activated polymer selected from the group consisting of polysaccharide, polyethylene glycol, polyvinylpyrrolidone and polyacid anhydride.

2. The derivative of claim 1, wherein the alkylene group is an ethylene radical.

3. The derivative of claim 2 wherein the polymer is a polysaccharide.

4. The derivative of claim 1 wherein oxidation is accomplished at pH 4–8 and a temperature of 0°–30° C.

5. The derivative of claim 1 wherein the polymer is a polysaccharide.

6. A process for the preparation of a water-soluble peroxidase derivative, comprising oxidizing peroxidase with periodic acid or with a salt thereof and binding the peroxidase to a water-soluble polymer selected from the group consisting of a polysaccharide, polyethylene glycol, polyvinylpyrrolidone and polyacid anhydride.

7. The process of claim 6, wherein binding takes place to an activated polymer.

8. The process of claim 6, wherein the peroxidase is oxidized at a temperature of about 0°–30° C. and a pH of about 4–8.

9. The process of claim 6, wherein the polymer used is a polysaccharide.

10. The process of claim 6, further comprising binding the oxidized peroxidase to the polymer by reacting the oxidized peroxidase with an alkylenediamine containing up to 8 carbon atoms to form a bridge to the polymer.

11. The process of claim 10, wherein the alkylenediamine is ethylenediamine and the polymer is activated polysaccharide.

12. The process of claim 6, wherein the peroxidase is oxidized at a temperature of 0–10° C. and pH of 5–6.

13. In a method of determining hydrogen peroxide using a peroxidase enzyme substrate to form a product which can be measured colorimetrically the improvement wherein the peroxidase is a water-soluble peroxidase derivative comprising peroxidase oxidized with periodic acid or a salt thereof and bound to a water-soluble polymer selected from the group consisting of a polysaccharide, polyethylene glycol, polyvinylpyrrolidone and polyacid anhydride.

14. A water soluble peroxidase derivative comprising peroxidase oxidized with periodic acid or a salt thereof and bound to a water-soluble activated polymer selected from the group consisting of polysaccharide, polyethylene glycol, polyvinylpyrrolidone and polyacid anhydride wherein the polymer is bound to the peroxidase through an ethylene group.

* * * * *